United States Patent
Lee et al.

(10) Patent No.: US 9,801,382 B2
(45) Date of Patent: Oct. 31, 2017

(54) METHOD FOR PREPARING EMULSIFIABLE SOLID AGROCHEMICAL COMPOSITION CONTAINING INORGANIC SALT

(71) Applicant: Kyung Nong Corporation, Seoul (KR)

(72) Inventors: Weon Kee Lee, Ulsan (KR); Jong Kwan Kim, Daejeon (KR); Jae Goon Lee, Gyeongsangbuk-do (KR); Hyeong Min Kim, Gyeongsangbuk-do (KR); In Cheon Hwang, Gyeongsangbuk-do (KR)

(73) Assignee: KYUNG NONG CORPORATION, Seoul (KR)

( * ) Notice: Subject to any disclaimer, the term of this patent is extended or adjusted under 35 U.S.C. 154(b) by 0 days.

(21) Appl. No.: 14/409,717

(22) PCT Filed: Jun. 26, 2013

(86) PCT No.: PCT/KR2013/005658
§ 371 (c)(1),
(2) Date: Dec. 19, 2014

(87) PCT Pub. No.: WO2014/003438
PCT Pub. Date: Jan. 3, 2014

(65) Prior Publication Data
US 2015/0189886 A1    Jul. 9, 2015

(30) Foreign Application Priority Data

Jun. 26, 2012 (KR) .................. 10-2012-0068549

(51) Int. Cl.
*A01N 25/12* (2006.01)
*A01N 57/12* (2006.01)
*A01N 25/14* (2006.01)
*A01N 43/653* (2006.01)
*A01N 53/00* (2006.01)

(52) U.S. Cl.
CPC ............. *A01N 57/12* (2013.01); *A01N 25/12* (2013.01); *A01N 25/14* (2013.01); *A01N 43/653* (2013.01); *A01N 53/00* (2013.01)

(58) Field of Classification Search
USPC ........................................... 514/127
See application file for complete search history.

(56) References Cited

U.S. PATENT DOCUMENTS 3,868,244 A * 2/1975 Taylor .................. C07D 403/12
504/155
4,310,520 A 1/1982 Narazaki
2009/0305889 A1* 12/2009 Cush ..................... A01N 25/04
504/101

FOREIGN PATENT DOCUMENTS

| CN | 101856018 A | 10/2010 |
|---|---|---|
| CN | 102187858 A | 9/2011 |
| FR | 2 290 844 A1 | 6/1976 |
| JP | 60-146803 | 8/1985 |
| JP | 02-108604 | 4/1990 |
| JP | 05-221803 | 8/1993 |
| JP | 2009-513610 | 4/2009 |
| KR | 10-2006-0001315 | 1/2006 |
| WO | WO 2004-014136 | 2/2004 |
| WO | WO 2006/058478 A1 | 6/2006 |
| WO | WO 2007-031251 | 3/2007 |
| WO | WO 2007/048851 A1 | 5/2007 |
| WO | WO 2011/012495 A1 | 2/2011 |

OTHER PUBLICATIONS

Search Report dated Nov. 24, 2015, for the corresponding European Application No. 13809268.9, in which references U1 and F1-F4 were cited.
Chinese Office Action dated Oct. 20, 2015, for the corresponding Chinese Application No. 201380034412.2, in which references F1-F2 were cited.
Japanese Office Action dated Apr. 5, 2016, for corresponding Japanese Patent Application No. 2015-520016, in which references F1-F3 were cited.

* cited by examiner

*Primary Examiner* — Johann R Richter
*Assistant Examiner* — Danielle Sullivan
(74) *Attorney, Agent, or Firm* — Saliwanchik, Lloyd & Eisenschenk

(57) ABSTRACT

The present invention relates to a method for preparing an emulsifiable solid agrochemical composition which contains an inorganic salt and which can be used as an agrochemical emulsion. The preparation method according to the present invention has the advantage that, because there is no need for a step of heating and evaporating a solvent or water, it is possible to use a surfactant or active ingredient that has a low boiling point or breaks down drastically at a high temperature, and, due to the solid-phase form, it is possible to minimise the amount that sticks to a container as there is no need to use a special synthetic resin or glass bottle that entails high packaging costs. Also, a granular emulsifier (EG) or a powdery emulsifier (EP) produced by means of the method according to the present invention can be further diluted in water before use so as to form common emulsion (EC) emulsified particles (0.1 μm to 100 μm) to transparent microemulsion particles (0.001 μm to 1 μm, or 1 nm to 1000 nm), and thus the emulsion size can be freely modified so as to maximise the activity of the agrochemical component in accordance with the characteristics of a crop or an insect pest.

8 Claims, No Drawings

METHOD FOR PREPARING EMULSIFIABLE SOLID AGROCHEMICAL COMPOSITION CONTAINING INORGANIC SALT

CROSS REFERENCE TO A RELATED APPLICATION

This application is a National Stage Application of International Application Number PCT/KR2013/005658, filed Jun. 26, 2013; which claims priority to Korean Patent Application No. 10-2012-0068549, filed Jun. 26, 2012; which are hereby incorporated by reference in their entirety, including all figures, tables and drawings.

FIELD OF THE INVENTION

The present invention relates to a method for preparing an emulsifiable solid agrochemical composition which contains an inorganic salt and can be used as an agrochemical emulsifiable concentrate.

BACKGROUND OF THE INVENTION

An emulsifiable concentrate (EC) is one of agrochemical formulations which have been most widely used since it has advantages in that it is easy to prepare and handle, and it may efficiently and economically deliver agrochemical active materials. The emulsifiable concentrate is prepared from oily active ingredients, or from active ingredients which may be dissolved in non-polar hydrocarbon solvents, for example, xylene, $C_9$-$C_{12}$ aromatic solvents, kerosene, or other proper solvents, and contains a surfactant to ensure excellent emulsion stability and spontaneous emulsification in spray tanks. However, the emulsifiable concentrate has a problem in that it is harmful to environments and human bodies since an excessive amount of a solvent is used in addition to the active materials of the agrochemicals and the surfactants.

To solve the above problems, formulations in which a solvent is used at a minimum amount and the other portion of the solvent is replaced with water have been developed. Such formulations include microemulsions (MEs), and oil-in-water emulsions (EWs). However, the formulations have problems in that they are more difficult to handle than solid formulations since they are in a liquid phase, and have poor stability which causes creaming, flocculation, ripening, and coalescence of the formulation since they are in a heterogeneous phase composed of water and oil. Also, the formulations have a problem in that a large amount of agrochemicals stick to the inner walls of containers upon packing in glass bottles or special synthetic resin containers, resulting in an increase in packaging costs.

To solve the above problems, Korean Patent No. 10-0432922 discloses a method which includes emulsifying an agrochemical active material in a minimum amount of a solvent and water and evaporating the water to obtain a solid emulsifiable concentrate. However, the method has problems in that the yield is low since the active material, the surfactant, and the like, which have a lower boiling point than the solvent or water, are evaporated during an evaporation process, and therefore it requires a special dryer which can be used to rapidly dry the active material at a temperature of 100° C. or less or lyophilize (cryosublimate) the active material, and it is difficult to prepare chemicals which severely break down at a high temperature.

Meanwhile, typical emulsifiable granules (EGs) or emulsifiable powders (EPs) include white granules having a particle diameter of 0.1 µm to 100 µm, and thus have a problem in that it is difficult to prepare a transparent microemulsion having a particle diameter of 0.001 µm to 1 µm (i.e., 1 nm to 1,000 nm) when the emulsifiable granules or powders are diluted in water.

BRIEF SUMMARY

Therefore, the present invention is designed to solve the problems of the prior art, and therefore it is an object of the present invention to provide a method for preparing an emulsifiable solid agrochemical composition in a simple manner without evaporating a solvent or water.

It is another object of the present invention to provide an emulsifiable solid agrochemical composition which is able to form granules having various granule sizes and exhibits excellent physical and biological properties.

According to an aspect of the present invention, there is provided a method for preparing an emulsifiable solid agrochemical composition, which includes (1) mixing an agrochemical active ingredient and a surfactant to prepare a liquid emulsifiable concentrate, and (2) mixing an inorganic salt with the liquid emulsifiable concentrate to adsorb the liquid emulsifiable concentrate onto the inorganic salt.

According to another aspect of the present invention, there is provided an emulsifiable solid agrochemical composition including an agrochemical active ingredient, a surfactant, and an inorganic salt.

The preparation method according to one exemplary embodiment of the present invention has advantages in that, because it does not require a step of heating and evaporating a solvent or water, it can be used to prepare an agrochemical composition including a surfactant or an active ingredient which has a low boiling point or severely breaks down at a high temperature, requires no need for the use of a glass bottle and a special synthetic resin container, which results in an increase in packaging costs, since the prepared agrochemical composition is in a solid-phase form, and can be useful in minimizing an amount the agrochemical composition sticking to the container. Also, when a emulsifiable granule (EG) or an emulsifiable powder (EP) prepared by means of the method according to one exemplary embodiment of the present invention is again diluted with water before use, emulsion particles (having a particle diameter of 0.1 µm to 100 µm) and transparent microemulsion particles (having a particle diameter of 0.001 µm to 1 µm, or 1 nm to 1,000 nm) of a typical emulsifiable concentrate (EC) may be formed, and thus the size of an emulsion can be freely changed so as to maximize the activities of agrochemical components according to the characteristics of crops or insect pests.

DETAILED DISCLOSURE

The present invention is directed to a method for preparing an emulsifiable solid agrochemical composition, which includes (1) mixing an agrochemical active ingredient and a surfactant to prepare a liquid emulsifiable concentrate, and (2) mixing an inorganic salt with the liquid emulsifiable concentrate to adsorb the liquid emulsifier onto the inorganic salt.

Hereinafter, the components used in the preparation method will be described in further detail.

(a) Agrochemical Active Ingredients

The selection of an agrochemical active ingredient is determined in advance according to desired applications. The agrochemical active ingredient that may be used in the present invention may be a pesticide or organic solvent-soluble pesticide, a fungicide or organic solvent-soluble fungicide, or a herbicide or organic solvent-soluble herbicide.

Examples of the pesticide or organic solvent-soluble pesticide include organic phosphates, for example Fonofos (Dyfonate; O-ethyl-S-phenyl-(R,S)-ethylphosphonodithioate), diazinon, malathion, parathion, etc.; piperonyl butoxide; synthetic pyrethroids, for example, halfenprox, bifenthrin, permethrin, and tefluthrin, bioresmethrin, resmethrin, zeta-cypermethrin, alpha-cypermethrin, etofenprox, deltamethrin, etc.; synthetic pyrethrin-type pesticides, for example, allethrin; organic phosphorus-based pesticides, for example profenofos, pyraclofos, ethoprophos, dimethylvinphos, terbufos, methidathion, dichlorvos, fosthiazate, phosphamidon, etc; pyrethrin; carbamates, for example aldicarb; benzoylurea-based pesticides, for example, chlorfluazuron, lufenuron, teflubenzuron, novaluron, diflubenzuron, etc.; benzoyl hydrazine-based pesticides, for example, tebufenozide, methoxyfenozide, etc.; diamide-based pesticides, for example, Flubendiamide, Chlorantraniliprole, Cyantraniliprole etc.; organic chlorine, for example, endosulfan; carbamate-based pesticides, for example, carbaryl (1-naphthyl N-methylcarbamate), methomyl, carbosulfan, BPMC, carbofuran, etc.; spinosyn-based pesticides, for example, spinosad, etc.; oxadiazine-based pesticides, for example, indoxacarb, etc.; thiadiazine-based pesticides, for example, buprofezin, etc.; and tolfenpyrad, but the present invention is not limited thereto.

Also, examples of the fungicide or organic solvent-soluble fungicide include aliphatic nitrogen fungicides; anilides; aromatic fungicides containing aromatic nitriles; benzimidazole and precursors thereof; carbamates; benzimidazole carbamate; chlorophenyl; conazoles; dicarboximide nitrophenyl; thiocarbamate and dithiocarbamate; imidazoles; morpholines; organic phosphorus fungicides; guanidine; hydroxyanilide; morpholines; oil, phenylamide; phenyl sulfide; phenylurea; pyridine; phthalimides; pyrimidine amides; pyrimidine; pyrimidinol; quinoline; quinone; quinoxaline; thiazole; strobilurins; triazole; xylylamine; various unclassified fungicides; morpholines, for example, fenpropidin, fenpropimorph, and tridemorph; piperalin; myclobutanil; conazoles, for example, difenoconazole, flusilazole, propiconazole, tebuconazole, triadimefon, etc.; pyridines, for example, pyrifenox; thiazoles, for example, etradiazole; organic phosphorus compounds, for example, phosdiphen; imidazoles, for example, pefurazoate; isoprothiolane; zoxamide; fenoxanil; tiadinil; strobilurins, for example, pyraclostrobin, orysastrobin, azoxystrobin; anilides, for example, boscalid, etc., but the present invention is not limited thereto.

Further, examples of the herbicide or organic solvent-soluble herbicide include chloroacetamides (i.e., dimethane amide) and chloroacetanilides, for example, acetochlor, pretilachlor, metachlor, butachlor, alachlor, metolachlor, diethatyl, metazachlor, dimethachlor, etc.; dichloroacetamides (i.e., dichlormid); butylates; cinmethylin; aryloxy phenoxy including fluazifop (e.g., fluazifop-P aryloxy phenoxy propionate); phenoxy and phenoxy derivatives, for example, phenoxy ester, phenoxy alkanoic acid, phenoxyacetic acid including 2,4-D ester; butylate, cyclolate, molinate, pebulate, thiobencarb, triallate, vernolate, s-ethyl dipropylcarbamothioate, thiocarbamate or carbamothioate including s-ethyl diethylcarbamothioate (etiolate); diethoate; cyclohexanedione or cyclohexanonedinitroaniline (isopropalin) including sethoxydim or clethodim; oximes (fluxofenim); aldehydes (acrolein), etc. Also, examples of the herbicide or organic solvent-soluble herbicide include naptalam and dicamba, benzoic acid and benzoic acid derivatives including 3,6-dichloro-o-anisic acid, and imidazolinyl benzoic acid, and esters and salts thereof; urea, for example, tebuthiuron; N-phenylphthalimide, for example, imides including Flumiclorac; phenoxy and phenoxy derivatives including phenoxy alkanoic acid or phenoxy acetic acid, for example, 2,4-D (2,4-dichlorophenoxy acetic acid), 3,4-DA (3,4-dichlorophenoxy acetic acid), 2,4-DB (4-(2,4-dichlorophenoxy)acetic acid), 3,4-DB (4-(3,4-dichlorophenoxy)butanoic acid), 2,4-DEB (2-(2,4-dichlorophenoxy)ethylbenzoate), 2,4-DEP (tris[2-(2,4-dichlorophenoxyl)ethyl] phosphite), MCPA acid (4-chloro-2-methylphenoxy acetic acid), MCPB acid (4-(4-chloro-2-methylphenoxy)butanoic acid), mecoprop, diclofop, diphenopenten, and dichloroprop; aryloxy phenoxy propionate, for example, fenoxaprop, haloxyfop, and quizalofop-P; benzothiazole acetic acid, for example, benazolin; dimethyl tetrachloroterephthalate (DCPA); amides and amide derivatives, for example, pronamide, propanil, and napropamide; acetamides, for example, mefluidide; benzamides, for example, isoxaben; chloroacetamide or chloroacetanilide, for example, propachlor; dinitroaniline, for example, benefin, oryzalin, and prodiamine; nitriles including benzonitrile and hydroxybenzonitrile, for example, bromoxynil, ioxynil, and dichlobenil; diphenyl ether or nitrodiphenyl ether, for example, acifluorfen, bifenox, fluoroglycofen, fomesafen, and oxyfluorfen; dithiocarbamate, for example, metham; carbamates including phenylcarbamate, for example, desmedipham, phenmedipham, and asulam; urea including phenylurea, for example, fluometuron, linuron, siduron, and diuron; pyridazinone, for example, norflurazon and pyrazon; pyridines, for example, dithiopyr and thiazopyr; pyridinone, for example, fluridone; pyridinecarboxylic acid or picolinic acid, for example, triclopyr, clopyralid, and picloram; oxadiazolidine, for example, methazole; and benzothiadiazole, for example, bentazone, etc.

The above-described agrochemical active ingredients may be used alone or in combination.

The agrochemical active ingredient may be used in an amount of approximately 0.1% by weight to approximately 50% by weight, preferably approximately 1% by weight to approximately 30% by weight, and more preferably approximately 1% by weight to approximately 20% by weight, based on the total amount of the emulsifiable composition.

(b) Surfactants

A surfactant that may be used in the present invention includes non-ionic surfactants, and ionic surfactants. These surfactants may be used alone or in combination.

Examples of the useful non-ionic surfactants include alkoxylated block polymers, alkoxylated alcohols, alkoxylated alkyl phenols; alkoxylated amines, alkoxylated amides; alkoxylated fatty esters; alkoxylated oils; fatty esters; alkoxylated fatty acids; sorbitan derivatives, etc.

Examples of the useful ionic surfactant include alkyl aryl sulfonates; alkyl aryl sulfonic acids; carboxylated alcohol ethoxylates, and alkyl phenol ethoxylates; carboxylic acid/fatty acid; diphenyl sulfonate derivatives; olefin sulfonates, phosphates and esters; phosphorus organic derivatives; quaternary surfactants; sulfates and sulfonates of oils and fatty acids; sulfates and sulfonates of ethoxylated alkyl phenols; sulfates of ethoxylated alcohols; sulfates of fatty esters; sulfonates of dodecyl and tridecylbenzene; sulfonates of naphthalenes and alkyl naphthalenes; sulfonates of petroleum; sulfosuccinamate; alkanolamide; and alkoxylated amines.

According to one exemplary embodiment of the present invention, alkoxylated alcohols and alkyl phenols, and most preferably surfactants including a hydrophobe having 4 to 50 ethylene oxide units and 4 to 16 carbon atoms may be used. According to one preferred exemplary embodiment of the present invention, polyethyleneglycol mono(tristyrylphenyl)ether may also be used as the surfactant.

The surfactant may adjust an emulsion type by adjusting a molar ratio of an ethylene oxide (EO)/propylene oxide (PO) addition product in a tristyrylphenyl group to adjust a hydrophilic-lipophilic balance (HLB) at 15/16/17.

Effective development of the surfactants requires selecting potential surfactants, performing emulsification tests according to methods known in the related art, and optimizing the performance of the most excellent surfactants. The selection of the potential surfactants depends on active types of agrochemicals, and solvents. Persons skilled in the related art may understand the importance of selection of the HLB and surfactants.

The surfactant according to one exemplary embodiment of the present invention may be used in an amount of 1 to 20% by weight, preferably 3 to 15% by weight, based on the total amount of the emulsifiable composition.

(c) Inorganic Salts

An inorganic salt according to one exemplary embodiment of the present invention is used as a carrier for adsorption. In this case, the inorganic salt according to one exemplary embodiment of the present invention may be used in the emulsifiable solid agrochemical composition to remarkably reduce an amount of the solvent which is harmful to environments and the human body. The inorganic salt according to one exemplary embodiment of the present invention adsorbs a liquid emulsifiable concentrate, which is composed of the agrochemical active ingredient and the surfactant, to form a solid phase. Therefore, a step of evaporating a solvent or water is not required upon preparation of conventional solid agrochemical drugs. As a result, the inorganic salt also has an advantage in that it is possible to use the surfactant or the agrochemical active ingredient having a low boiling point.

Further, when the inorganic salt is in a powdery phase, the inorganic salt may be used to form an emulsifiable powder (EP), and, when the inorganic salt is in a granular phase, the inorganic salt may be used to form an emulsifiable granule (EG). The emulsifiable granule may be prepared by granulating the inorganic salt in a powdery phase.

Examples of the inorganic salt suitable for use in the present invention include sodium carbonate ($Na_2CO_3$), anhydrous sodium carbonate, sodium hydrogen carbonate ($NaHCO_3$), sodium percarbonate ($2Na_2CO_3 \cdot 3H_2O_2$), calcium chloride ($CaCl_2$), sodium phosphate ($Na_2HPO_4$), anhydrous sodium phosphate, potassium carbonate ($K_2CO_3$), anhydrous potassium carbonate, potassium hydrogen carbonate ($KHCO_3$), potassium phosphate ($K_3PO_4$), anhydrous potassium phosphate, sodium sulfate ($Na_2SO_4$), anhydrous sodium sulfate, and ammonium persulfate (($NH_4)_2S_2O_8$), but the present invention is not limited thereto. More preferably, sodium carbonate or potassium carbonate may be used herein. The inorganic salts may be used alone or in combination.

The inorganic salt may be used in an amount of 50 to 95% by weight, preferably 60 to 95% by weight, based on the total amount of the emulsifiable solid composition.

The method for preparing an emulsifiable solid agrochemical composition according to one exemplary embodiment of the present invention may further include dissolving the agrochemical active ingredient in a solvent before mixing the agrochemical active ingredient with the surfactant when the agrochemical active ingredient is in a solid phase. Hereinafter, the solvents used to dissolve the agrochemical active ingredient will be described.

(d) Solvents

Proper solvent systems are selected in consideration of the solubility of the agrochemical active ingredient, and the chemical and toxicological profile of the solvent. The solvent includes solvents tested by the Environmental Protection Agency (EPA, US), and examples of the solvent include aliphatic paraffin oils, for example, kerosene or purified paraffin; aromatic solvents, for example, xylene; $C_9$-$C_{12}$ aromatic solvents, for example, AROMATIC 100, 150, and 200 (Exxon Chemical), ISOPAR L, SOLVESSO 100, 150, and 200, KOCOSOL 100, 150, and 200 (SK Chemical); chlorinated hydrocarbons, for example, chlorobenzene; alcohols, for example, butanol, and benzyl alcohol; ketones, for example, cyclohexanone, and N-methyl pyrrolidone; carbonates, for example, methylene carbonate, ethylene carbonate, butylene carbonate, and propylene carbonate; and ethers, for example, diethylene glycol, and diethoxol; vegetable oils; methylated vegetable oils; petroleum oils; and sugar fatty acid esters, for example, sucrose ester, etc., but the present invention is not limited thereto. Preferably, $C_9$-$C_{12}$ hydrocarbon solvents which are inexpensive and can be used to dissolve a large amount of the agrochemical active ingredient may be used herein.

The solvent may be used in an amount of 1 to 30% by weight, preferably 1 to 20% by weight, based on the total amount of the emulsifiable composition.

The emulsifiable solid agrochemical composition according to one exemplary embodiment of the present invention may further include an additive according to a purpose of use. Examples of the additive that may be used in the present invention include a spreading agent, a penetrating agent, a drift control agent, an anti-degrading agent, a stabilizing agent, an anti-foaming agent, a binding agent, and a pH buffer solution, but the present invention is not limited thereto. The additive may be used at a small amount, preferably used in an amount of 5% by weight or less, based on the total amount of the emulsifiable composition.

The emulsifiable solid agrochemical composition according to one exemplary embodiment of the present invention may be diluted with water, and then coated onto a target product using any proper method, for example, spraying, dipping, or rubbing.

EXAMPLES

Hereinafter, the present invention will be described in further detail with reference to Examples. However, it should be understood that the Examples are not intended to limit the scope of the present invention.

Examples 1 to 5 and Comparative Examples 1 and 2

Preparation of Drugs 1,000 g of drugs of Examples 1 to 5 and Comparative Examples 1 and 2 were respectively prepared according to compositions as listed in the following Table 1. In the case of the drug of Examples 1 to 4 in which an active ingredient was in a solid phase, the agrochemical active ingredient was dissolved in a mixed solvent of organic solvents, and then mixed with a surfactant to prepare a liquid emulsifiable concentrate. The liquid emulsifiable concentrate was sprayed and adsorbed onto an inorganic salt at room temperature for 10 minutes using a sprayer to prepare drugs. In the case of the drug of Example 5 in which the active ingredient was in a liquid phase, an agrochemical active ingredient and a surfactant were mixed to prepare a liquid emulsifiable concentrate, and the liquid emulsifiable concentrate was then sprayed and adsorbed onto an inorganic salt to prepare a drug. In the case of the drugs of Comparative Examples 1 and 2, the drugs were prepared without using an inorganic salt.

Experimental Example 1

Analysis of Physical Properties

The physical properties of the drugs of Examples 1 to 5 and Comparative Examples 1 and 2 were compared, as follows.

(1) Observation of emulsion types of drugs: 100 mL of 3° hard water was added to 100-mL test tubes, the drugs of Examples and Comparative Examples were added in an amount of 1 mL, respectively, and the emulsion types were observed with the naked eye.

(2) Emulsion stability test for drugs: 95 mL of 3° hard water (30±2° C.) was added to 100-mL cylinders, the drugs of Examples and Comparative Examples were added in an amount corresponding to the maximum concentration of drug preparations used, 3° hard water was added to a final volume of 100 mL, and the resulting mixture was emulsified by strongly shaking the cylinders three times. Thereafter, the emulsified solution was kept constant in a 30±2° C. thermostatic bath, and the uniformity of the emulsified solution, separation of oily products or clots, and the like were observed after 2 hours.

(3) Room-temperature stability test for drugs: The drugs were added to single-layered resin containers, and stored at room temperature (20° C.) for 4 weeks, and the appearance of the storage containers was then observed.

(4) High-temperature stability test for drugs: The drugs were added to single-layered resin containers, and stored at 50° C. for 4 weeks in an oven, and the appearance of the storage containers was then observed.

(5) Container adhesion test for drugs: A pourability test was used to examine an amount of a drug adhered to a container. The weights (A) of 100-mL Erlenmeyer flasks with caps were measured, the drugs were added to the flasks until 20% (20 mL of a liquid phase, or 20 g of a solid phase) of the containers were filled with the drugs, the caps were closed, and the weights (B) of the flasks were measured. The drugs were kept constant for 24 hours, the caps were opened, the Erlenmeyer flasks were tilted at an angle of 45° for 60 seconds to pour the respective drugs, and the remaining drugs were completely poured by keeping the Erlenmeyer flasks standing upside down for 60 seconds. After the respective drugs were poured, the weights (C) of the Erlenmeyer flasks with caps were measured. In this case, the adhesion (D) of the drug remaining in the container was calculated using the equation: (D=(C−A)/(B−A)×100%).

The test results are listed in the following Table 1.

TABLE 1

| | | Examples | | | | | Comparative Examples | |
|---|---|---|---|---|---|---|---|---|
| | | 1 | 2 | 3 | 4 | 5 | 1 | 2 |
| Drug | Difenoconazole | 5.0 | 5.0 | 5.0 | — | — | 5.0 | — |
| | Deltamethrin | — | — | — | 2.0 | — | — | 2.0 |
| | Terbufos | — | — | — | — | 4.5 | — | — |
| Surfactant | NK-TP150R | 5.0 | — | — | 4.0 | 7.0 | 5.0 | 4.0 |
| | NK-TP200R | — | 5.0 | — | — | — | — | — |
| | NK-TP250R | — | — | 5.0 | — | — | — | — |
| Solvent | NMP | 1.5 | 1.5 | 1.5 | 2.0 | — | 1.5 | 2.0 |
| | BC | 4.0 | 4.0 | 4.0 | 6.0 | — | 87.5 | 92.0 |
| Inorganic salt | $Na_2CO_3$ | 83.5 | 83.5 | 83.5 | 86.0 | 88.5 | — | |
| Total amount | | 100.0 | 100.0 | 100.0 | 100.0 | 100.0 | 100.0 | 100.0 |
| Emulsion type | (100 × dilution) | ME | DC | EC | ME | ME | EC | EC |
| Emulsion stability | (after 2 hours) | Good | Good | Good | Good | Good | Good | Good |
| Room-temperature stability (20° C.: stored for 4 weeks) | Container deformed | Not deformed | Not deformed | Not deformed | Not deformed | Not deformed | Not deformed | Not deformed |
| High-temperature stability (50° C.: stored for 4 weeks) | Container deformed | Not deformed | Not deformed | Not deformed | Not deformed | Not deformed | Container shrunk | Container shrunk |
| Container adhesion | (%) | 0.2 | 0.2 | 0.2 | 0.2 | 0.2 | 4.5 | 3.8 |

NMP: N-methyl pyrrolidone

BC: Butylene carbonate

NK-TP150R/200R/250R: polyethyleneglycol mono(tristyrylphenyl)ether

ME: Microemulsion

DC: Dispersion concentrate

EC: Emulsifiable concentrate

As listed in Table 1, it could be seen that, in the case of Examples 1 to 3 in which the active ingredient was a fungicide, the emulsion types were observed to be ME, DC, and EC when the drugs were diluted 100 times by changing the types of polyethyleneglycol mono(tristyrylphenyl) ethers, indicating that it was easy to control the particle diameter of the drugs to be emulsified. Also, it could be seen that, in the case of Example 5 in which the active ingredient was in a liquid phase, the drugs were prepared into ME having a small particle size without using a solvent.

Meanwhile, the drugs containing an inorganic salt according to one exemplary embodiment of the present invention had good stability in the high-temperature stability test, but the single-layered resin containers were shrunk in the case of Comparative Examples 1 and 2. Also, in the container adhesion test, the drugs of Examples 1 to Example 5 were adhered to the inner walls of the containers at a smaller amount than those of the drugs of Comparative Examples 1 and 2.

The results showed that the physical properties of the drugs were improved when the inorganic salt was mixed with the drugs.

Experimental Example 2

Analysis of Biological Properties

<2-1> Biological Drug Efficacy Test for Pesticides

Drug efficacy tests were performed to determine whether the drugs of Example 4 and Comparative Example 2 whose emulsion types were different with ME and EC were effective against Phyllonorycter ringoniella.

An appraised crop, apple (Fuji apple), was completely randomized every weeks to perform a drug efficacy test in triplicate. In the drug efficacy test, the drug was diluted 2,000 times, and sprayed twice on cauline leaves at an interval of 7 days at an early stage of outbreak of *P. ringoniella*. The test were performed by examining 300 apple tree leaves per test group that were damaged by *P. ringoniella* larvae at points of time of 7 and 14 days after final drug treatment. The test results are listed in the following Table 2. In this test, the control value was calculated using the following equation.

$$\text{Control value} = \frac{\left(\begin{array}{c}\text{average damaged leaves in untreated group} - \\ \text{average damaged leaves in treated group}\end{array}\right)}{\text{average damaged leaves in untreated group}} \times 100$$

The test results are listed in the following Table 2.

more without any drug damage of the appraised crops after 14 days of drug treatment, but the drug of Comparative Example 2 had no drug damage to the appraised crop (see Table 3) but had a low control value of less than 90%.

<2-2> Biological Drug Toxicity Test for Pesticides

To perform a biological drug toxicity test on the drug of Example 4, an apple (Fuji apple) was selected as the appraised crop to perform a drug toxicity test according to each prescription. A completely randomized method was performed in triplicate to randomize a tested group, and each drug was sprayed on cauline leaves at a recommended amount and a double amount. A far-sighted view survey was performed on drug damage at points of time of 7, 14, and 21 days. The results are listed in the following Table 3.

TABLE 3

| Item | Dilution (times) | *Drug damage degree (0 to 5) | | |
|------|------------------|------|------|------|
| | | 7 days | 14 days | 21 days |
| Example 4 | 1,000 | 0 | 0 | 0 |
| | 2,000 | 0 | 0 | 0 |

*0: Leaves are not damaged by drug when observed with the naked eye.
1: Leaves are very slightly damaged by drug with small leaf burn formed.
2: A small part of treated leaves are damaged by drug.
3: 50% of treated leaves are damaged by drug.
4: Leaves are severely damaged by drug, but healthy leaves are still left intact.
5: Leaves are severely damaged and withered by drug.

As listed in Table 3, it was revealed that the drug of Example 4 did not cause drug damage to the apple upon recommended and double dilutions, and thus was not harmful to the apple. In the summary of Experimental Examples <2-1> and <2-2>, it could be seen that the drugs according to one exemplary embodiment of the present invention did not cause drug damage to the appraised crop at a point time of 14 days of drug treatment, and showed an excellent biological effect since it had a control value of 90% or more against the appraised insect.

<2-3> Biological Drug Efficacy Test for Fungicides

Drug efficacy tests were performed to determine whether the drugs of Example 1 and Comparative Example 1 whose emulsion types were different with ME and EC were effective against Sphaerotheca fuliginea.

A randomized block method was performed in triplicate in the experimental field, in which *S. fuliginea* naturally occurred from the 14th day after cucumber planting, to randomize a tested group, and the drugs of Example 1 and Comparative Example 1 were sprayed three times on cauline leaves at an interval of 10 days in the first stage of the

TABLE 2

| Items | Dilution (times) | Damaged leaves 7 days after final drug treatment (%) | | | | | Damaged leaves 14 days after final drug treatment (%) | | | | |
|-------|------------------|------|------|------|------|------|------|------|------|------|------|
| | | Once | Duplicate | Triplicate | Average | Control value | Once | Duplicate | Triplicate | Average | Control value |
| Example 4 | 2,000 | 0.7 | 0.0 | 0.7 | 0.4 | 95.0 | 1.3 | 0.3 | 1.0 | 0.9 | 92.3 |
| Comparative Example 2 | 2,000 | 2.0 | 1.0 | 1.0 | 1.3 | 83.8 | 2.7 | 1.7 | 1.7 | 2.0 | 82.9 |
| Untreated | — | 8.0 | 9.3 | 6.7 | 8.0 | — | 10.7 | 11.7 | 12.7 | 11.7 | — |

* The percentage (%) of damaged leaves in the untreated group should be greater than 5% per spraying to be approved as an experimental value.

As listed in Table 2, it was revealed that the drug of Example 4 had a more excellent control value against P. ringoniella than the drug of Comparative Example 2, and that the drug of Example 4 had a control value of 90% or outbreak to compare the medicinal effects. After 10 days of the final drug treatment, an outbreak degree of S. fuliginea in each test group was examined, and the control value was calculated. The results are listed in the following Table 4.

TABLE 4

| Tested drug | Dilution (times) | Outbreak degree | | | | DMRT | Control value |
|---|---|---|---|---|---|---|---|
| | | Once | Duplicate | Triplicate | Average | | |
| Example 1 | 1,500 | 4.6 | 5.2 | 3.3 | 4.4 | a | 90.0 |
| Comparative Example 1 | 1,500 | 12.1 | 12.7 | 14.3 | 13.0 | b | 70.3 |
| Untreated | — | 41.1 | 51.4 | 38.9 | 43.8 | c | — |

* The minimum outbreak degree in the untreated group should be greater than or equal to 20 to be approved as an experimental value.

As listed in Table 4, it was revealed that the drug of Example 1 had an excellent control value of 90% against S. fuliginea, but the drug of Comparative Example 1 had a poor control value of 70.3%.

<2-4> Biological Drug Toxicity Test for Fungicides

To perform a biological drug toxicity test on the drug of Example 1, a cucumber was selected as the appraised crop to perform a drug toxicity test according to each prescription. A randomized block method was performed in triplicate to randomize a tested group, and the drugs were sprayed on the cauline leaves of cucumber at a recommended amount and a double amount according to each prescription. Thereafter, a far-sighted view survey was performed on drug damage at points of time of 3, 5, and 7 days. The results are listed in the following Table 5.

TABLE 5

| Tested drug | Dilution (times) | Drug damage degree | | | Drug damage |
|---|---|---|---|---|---|
| | | $3^{rd}$ day | $5^{th}$ day | $7^{th}$ day | |
| Example 1 | 750 | 0 | 0 | 0 | None |
| Example 1 | 1,500 | 0 | 0 | 0 | None |

*0: Leaves are not damaged by drug when observed with the naked eye.
1: Leaves are very slightly damaged by drug with small leaf burn formed.
2: A small part of treated leaves are damaged by drug.
3: 50% of treated leaves are damaged by drug.
4: Leaves are severely damaged by drug, but healthy leaves are still left intact.
5: Leaves are severely damaged and withered by drug.

As listed in Table 5, it was revealed that the drug of Example 1 did not cause drug damage to the cucumber upon recommended and double dilutions. Also, it was confirmed that, at points of time of 3, 5, and 7 days after the drug was sprayed on shoots, flowers, fruits, and cauline leaves of the cucumber crop, the drug damage of the cucumber crop was examined, but the drug of Example 1 did not cause drug damage to the cucumber, and thus was not harmful to the cucumber.

In the summary of Experimental Examples <2-3> and <2-4>, it could be seen that the drugs according to one exemplary embodiment of the present invention did not cause drug damage to the appraised crop, and had an excellent control value.

While the invention has been shown and described with reference to certain exemplary embodiments thereof, it will be understood by those skilled in the art that various changes in form and details may be made therein without departing from the spirit and scope of the invention as defined by the appended claims.

The invention claimed is:

1. A method for preparing an emulsifiable solid agrochemical composition without heating and evaporating a solvent or water, comprising:
   (1) mixing an agrochemical active ingredient and a surfactant to prepare a liquid emulsifiable concentrate; and
   (2) adsorbing the liquid emulsifiable concentrate onto an inorganic salt;
   wherein the inorganic salt is selected from the group consisting of sodium carbonate ($Na_2CO_3$), anhydrous sodium carbonate, sodium hydrogen carbonate ($NaHCO_3$), sodium percarbonate ($2Na_2CO_3 \cdot 3H_2O_2$), calcium chloride ($CaCl_2$), sodium phosphate ($Na_2HPO_4$), anhydrous sodium phosphate, potassium carbonate ($K_2CO_3$), anhydrous potassium carbonate, potassium phosphate ($K_3PO_4$), anhydrous potassium phosphate, sodium sulfate ($Na_2SO_4$), anhydrous sodium sulfate, ammonium persulfate (($NH_4)_2S_2O_8$), and a mixture thereof;
   wherein the inorganic salt is used in an amount of 60 to 95% by weight, based on the total amount of the composition.

2. The method of claim 1, wherein the agrochemical active ingredient is a pesticide, a fungicide or a herbicide.

3. The method of claim 1, wherein the surfactant is a non-ionic surfactant, or an ionic surfactant.

4. The method of claim 1, wherein the inorganic salt is sodium carbonate or potassium carbonate.

5. The method of claim 1, further comprising:
   dissolving the agrochemical active ingredient in a solvent before mixing the agrochemical active ingredient with the surfactant when the agrochemical active ingredient is in a solid phase.

6. The method of claim 5, wherein the solvent is selected from the group consisting of an aliphatic paraffin oil, an aromatic solvent, a chlorinated hydrocarbon, an alcohol, a ketone, N-methyl pyrrolidone, a carbonate, an ether, a vegetable oil, a methylated vegetable oil, petroleum oil, a sugar fatty acid ester, and a mixture thereof.

7. The method of claim 1, wherein the inorganic salt is selected from potassium carbonate ($K_2CO_3$) and anhydrous potassium carbonate.

8. The method of claim 1, wherein the inorganic salt has an oil absorbency of 10% to 47%.

* * * * *